United States Patent

Malczewski et al.

[11] Patent Number: 5,831,728
[45] Date of Patent: Nov. 3, 1998

[54] GAS EMISSION SPECTROMETER AND METHOD

[75] Inventors: Mark Leonard Malczewski, North Tonawanda; Hollis Clifford Demmin, Tonawanda; David Elston Brown, Lockport; Donald Richard Wiltse, Wilson, all of N.Y.

[73] Assignee: Praxair Technology, Inc., Danbury, Conn.

[21] Appl. No.: 812,291

[22] Filed: Mar. 7, 1997

Related U.S. Application Data

[63] Continuation of Ser. No. 384,043, Feb. 6, 1995, abandoned, which is a continuation of Ser. No. 36,163, Mar. 24, 1993, Pat. No. 5,412,467.

[51] Int. Cl.$^6$ .................................................. G01J 3/30
[52] U.S. Cl. ........................ 356/316; 356/311; 356/326
[58] Field of Search ................................. 356/311, 316, 356/326, 314, 417; 250/288

[56] References Cited

U.S. PATENT DOCUMENTS

| | | | |
|---|---|---|---|
| 2,943,223 | 6/1960 | Fay | 313/201 |
| 3,032,654 | 5/1962 | Fay et al. | 250/43.5 |
| 3,645,629 | 2/1972 | Dagnall | 356/315 |
| 4,801,209 | 1/1989 | Wadlow | 356/417 |
| 5,036,204 | 7/1991 | Leyden | 356/354 |
| 5,135,604 | 8/1992 | Kumar et al. | 356/316 |
| 5,394,236 | 2/1995 | Murnick | 356/311 |

OTHER PUBLICATIONS

Holman et al., "Optical Emission Spectroscopy with a Microwave–Induced Plasma in a Sealed Microtube", Tazanna, vol. 29, No. 5, May 1992, pp. 419–421.

"Emission Spectromeyric Method and Analyzer for Traces of Nitrogen in Oxygen" Analytical Chemistry, vol. 34, No. 10, Sep. 1962, pp. 1254–1260, Fay, Homer, Mohr, Paul H. and Cook, Gerhard A.

Primary Examiner—David B. Hardy
Attorney, Agent, or Firm—Bernard Lau

[57] ABSTRACT

A gas emission spectrometer and method for analyzing a continuously flowing gas stream using gas emission spectroscopy to measure low concentration levels of one or more gas/vapor impurities in the gas stream. Alternating power is applied to an electric discharge source to generate emissive radiation which is filtered into an optical signal at the emission wavelength of a preselected impurity gas. The optical signal is converted into an electrical signal which is selectively amplified within a narrow frequency range centered at substantially twice the excitation frequency of the alternating power source. The impurity concentration is measured from the amplified signal upon rectification.

5 Claims, 3 Drawing Sheets

GAS EMISSION SPECTROMETER AND METHOD

This application is a Continuation of prior U.S. application Ser. No. 08/384,043 filing date Feb. 6, 1995, now abandoned, and which is a continuation of application Ser. No. 08/036,163 filing date Mar. 24, 1993, now U.S. Pat. No. 5,412,467.

FIELD OF THE INVENTION

This invention relates to a gas emission spectrometer and method for analyzing a gas stream to detect and quantify the concentration of one or more predetermined gaseous contaminants in a gas stream of mixed gases under continuous flow conditions and more particularly to an improved gas emission spectrometer and method for analyzing a gas stream to determine the concentration of one or more preselected gaseous contaminants at low concentration levels in the parts per billion range with high accuracy.

BACKGROUND OF THE INVENTION

An ultra high purity supply of inert gas, particularly argon, has become essential in the manufacture of large scale integrated circuits. Semiconductor manufacturers utilize commercial purifiers to remove impurities in the argon stream to less than 10 parts per billion (ppb). Some of the more important impurities removed by these purifiers include $O_2$, $H_2O$, CO, $H_2$, $CO_2$, $CH_4$, and $N_2$. Continuous monitoring of the inert gas stream under continuous flow conditions to assure that the gas stream purity continues to meet its stringent specifications is mandatory. With the exception of nitrogen, analytical instruments presently exist which are able to satisfy the required <10 ppb mimimum detection limit (MDL). Nitrogen is also the most likely impurity to "break through" the commercial purifier system and contaminate the high purity gas stream.

Currently the only method for continuous monitoring of nitrogen at low concentration levels in a high purity argon gas stream is emission spectroscopy. In emission spectroscopy the gases are excited in a gaseous discharge to produce optical emission lines characteristic of each gas in the gas stream. The emission line for nitrogen is then isolated and analyzed to measure its intensity in order to quantify its concentration. To date, this method is however limited to a minimum detection limit (MDL) for nitrogen in the range of 0.1–0.5 ppm(100–500 ppb).

The conventional emission spectrometer employs a dielectric quartz tube having two electrodes extending therefrom to which an alternating electric field is applied at a high potential sufficient to cause an electric discharge. The gas sample is fed into the tube under continuous flow conditions and is excited by absorption of energy during the electric discharge. This results in the emission of radiant energy as the gas molecules drop from an elevated energy level to lower energy levels. The wavelengths of this emission are characteristic of the gas components excited by the absorption and release of energy. By filtering out unwanted wavelengths the intensity of the emission of any gas in the gas stream can be measured. In an argon gas stream, the concentration level of an impurity gas such as nitrogen can be measured by optically isolating light at the strongest characteristic wavelength for nitrogen i.e. at 337.1 nm and converting the separated optical signal to a corresponding electrical signal.

In conventional emission spectroscopy, the radiated output signal from the electric discharge source is modulated to produce an alternating signal using a mechanically rotating wheel sometimes colloquially referred to as a "chopper". The chopper, thus used to modulate the optical signal output from the electric discharge tube, produces a desired modulation frequency of e.g. 510 Hz. The modulated signal is then filtered to isolate the emission line 337.1 nm which is detected at the modulated frequency using signal electronics which includes a tuned amplifier to selectively amplify the 510 Hz modulated frequency signal and to reject other frequencies. A chopper has been used in emission spectroscopy for modulating the optical signal output of the silent electric discharge tube from its early inception. The function and need for a chopper in emission spectroscopy is described in detail in U.S. Pat. No. 3,032,654 issued May 1, 1962.

SUMMARY OF THE INVENTION

In accordance with the present invention it has been discovered that the use of a "chopper" and its function, which heretofore was deemed essential to the operation of an emission spectrometer, may be entirely eliminated. Instead the emissive radiation from the electric discharge source is filtered to form an optical signal having a narrow radiation emission bandwidth which is directly converted into an electrical signal and amplified within a narrow frequency range centered at substantially twice the excitation frequency of the source of alternating voltage applied across the electric discharge source. This has been found to increase the sensitivity of detection of any gaseous impurity in the gas sample by an order of magnitude. In particular the range of detection of nitrogen in an argon gas sample using the present invention is extended to a level below 20 parts per billion (ppb).

The method of the present invention for analyzing a continuously flowing gas stream to detect the presense of a gas or vapor impurity in the gas stream at concentration levels extending below 20 parts per billion using emission spectroscopy comprises the steps of:

directing a sample of the gas stream through an electric discharge source;

applying an alternating source of power across said electric discharge source at a preselected excitation frequency with said alternating power source having a peak voltage sufficient to sustain an electric discharge and to generate a wide radiation spectrum of emissive radiation from said gas stream;

filtering said radiation spectrum to form an optical signal having a narrow radiation emission bandwidth corresponding to the stronger emission wavelength(s) of a preselected gas or vapor impurity to be analyzed;

converting said optical signal into an electrical signal;

selectively amplifying said electrical signal within a narrow frequency range centered at substantially twice said excitation frequency; and analyzing said selectively amplified electrical signal to determine the concentration level of the gas or vapor under analysis.

The present invention also relates to an improved gas emission spectrometer for analyzing and measuring low concentration levels of one or more gas/vapor impurities in a gas stream under continuous flow conditions comprising: a silent electric discharge source; means for feeding a gas sample through said discharge source at a preselected flow rate; power supply means for applying a source of alternating voltage across said silent discharge tube at a predetermined excitation frequency and of sufficient peak voltage predetermined excitation frequency and having sufficient peak voltage to sustain an electric discharge and generate emissive radiation from said gas stream over a wide radiation spectrum; means for optically filtering said radiation spectrum to form an optical signal having a narrow radiation emission bandwidth corresponding to the stronger emission wavelength(s) of a preselected gas impurity for detection in said gas sample; means for converting said optical signal into a corresponding electrical signal and analog amplifier means for selectively amplifying said electrical signal within a narrow frequency range centered at substanially twice the excitation frequency whereby the sensitivity of detection of said gas impurity is increased to a minimum detection level (MDL) of below 20 parts per billion (ppb). It should be noted however, that the method of the invention is not limited to a sensitivity range with an MDL of below 20 ppb and, in fact, may be used in other applications where sensitivity is not as critical and with an MDL only in the parts per million (ppm) range.

BRIEF DESCRIPTION OF THE DRAWINGS

Other advantages of the present invention will become apparent from the following detailed description of the invention when read in conjunction with the accompaning drawings of which.

DETAILED DESCRIPTION OF THE INVENTION

Figure 1:
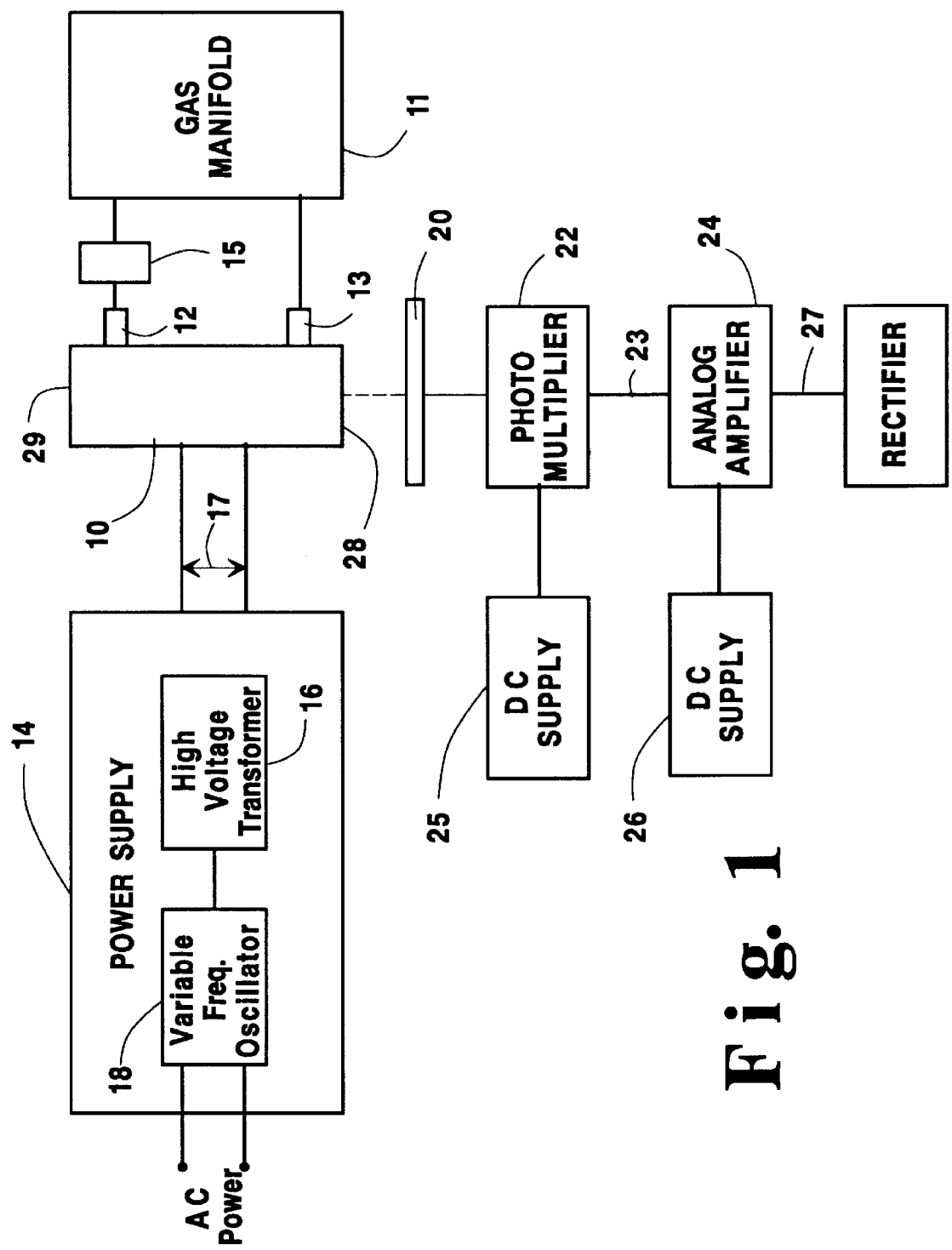
FIG. 1 is a schematic block diagram of the emission spectrometer of the present invention.

The emission spectrometer of FIG. 1 comprises an electric discharge analyzer tube 10 through which a sample of a gas to be analyzed is passed under continuous flow conditions from a manifold or gas supply 11. The electric discharge analyzer tube 10 may represent any conventional discharge source capable of sustaining an electric discharge upon the application of an electric field. The preferred electric discharge analyzer tube 10 is a "silent electric discharge tube" based upon the principles taught by H. Fay in U.S. Pat. No. 2,943,223 the disclosure of which is herein incorporated by reference. A large part of the light emitted from a silent electric discharge tube is directed in one direction and is approximately parallel light.

The silent electric discharge analyzer tube 10 is of conventional design using the teaching of the aforementioned Fay patent. In general the analyzer tube 10 is composed of a glass quartz tube which has been flatened on a mandrel to form a rectangular geometry with flat sides to which electrodes are attached. The electrodes extend outside the tube 10 and are connected to an input power supply 14 including a high voltage ionization transformer 16 and a variable frequency oscillator 18. Line votage from a conventional AC line supply of e.g. 120 volt 60 Hz, is connected to the variable frequency oscillator 18 of the input power supply 14. The variable frequency oscillator 18 may be of any conventional design which permits adjustment of the frequency of the output 17 of the power supply 14 (hereinafter referred to as the "excitation frequency") applied to the electric discharge tube 10. The excitation freqency may be adjusted from a ratio of one to one relative to the AC line supply frequency to any desired multiple or fraction thereof. The high voltage ionization transformer 16 is also conventional in design and steps up the output voltage of the input power supply 14 to the required voltage necessary to sustain an electric discharge between the electrodes in the electric discharge analyzer tube 10. The required voltage necessary to sustain an electric discharge is typically of the order of many thousands of volts. Accordingly, the ionization transformer 16 must be able to multiply the line voltage by a large multiple of e.g. 60 for a line voltage of 120 volts to provide a typical input voltage of 7200 volts.

The analyzer tube 10 has an input port 12 and an output port 13 for passing a sample of gas through the analyzer tube 10 at a controlled flow rate. An adjustable valve 15 may be used to adjust the pressure and rate of flow of the sample gas from the gas supply manifold 11 into the analyzer tube 10 to within a more desirable flow range of typically between 1–4 SCFH at atmospheric pressure. Any gas composition may be analyzed in the analyzer tube 10 under continuous flow conditions by the method of the present invention provided it has an optical emission characteristic which permits detection by emission spectroscopy.

An optical filter 20 is used to isolate the emission line of the gas impurity to be analyzed. The optical filter 20 must therefore have a very narrow bandpass to eliminate the broad spectrum of light emitted from the silent electric discharge source 10. For example, to detect nitrogen in a gas sample of argon the emission line of interest is 337.1 nm.

A photomultiplier 22, of conventional design, is used to convert the isolated optical signal transmitted from the optical filter 20 to a corresponding electrical output signal 23. The photomultiplier 22 should have a maximum spectral response near the emission line of interest for the impurity gas to be detected.

The electrical output signal 23 from the photomutiplier 22 may be fed to any conventional analog amplifier 24 capable of selectively amplifying the signal 23 within a narrow range of frequencies centered, in accordance with the present invention, at approximately twice the excitation frequency of the input power supply 14. The analog amplifier 24 may represent a conventional "lock-in" amplifier as is known to those skilled in the art which amplifies the signal at a frequency corresponding to an adjustable reference frequency signal to be set at twice the excitation frequency or may be represented by a "tuned amplifier" which acts to select a very narrow frequency band out of the electrical signal 23 which for the present invention would be equal to approximately twice the excitation frequency of the input power supply 14. A conventional "tuned amplifier" design includes one or more operational amplifiers, with its maximum response centered or "tuned" to equal twice the excitation frequency of the input power supply 14. Accordingly, the analog amplifier 24 will amplify signals only at approximately twice the excitation frequency of the input power supply 14. Separate DC power supplies 25 and 26 provide power for the photomultiplier 22 and the analog amplifier 24 respectively.

The output signal 27 from the analog amplifier 24 is rectified into a DC signal which provides an indication of the magnitude of the level of gas impurity for display on a monitor and/or for driving a recorder which may be calibrated for the analysis of a specific impurity measurement.

Figure 2A:
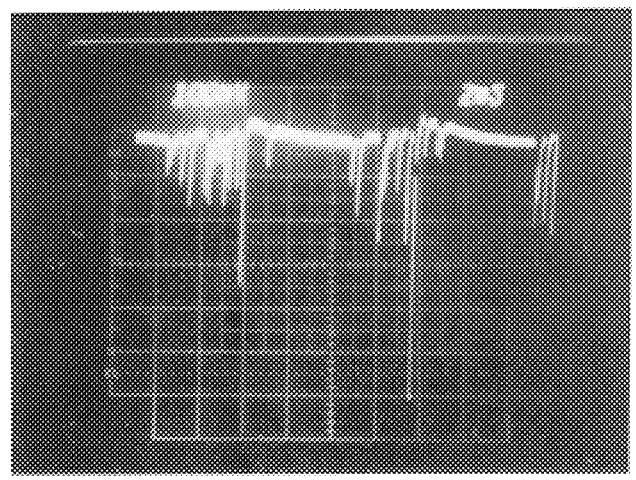
FIG. 2A shows an oscillograph trace of an electrical signal corresponding to the optical emission from the silent discharge tube of FIG. 1 at an excitation frequency of 60 Hz.
Figure 2B:
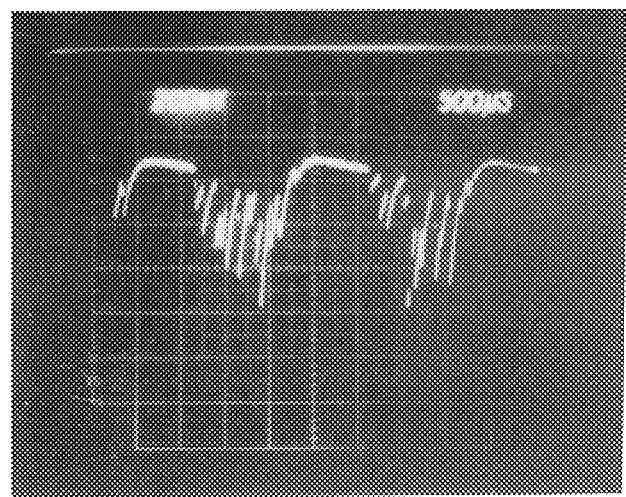
FIG. 2B shows an oscillograph trace similar to FIG. 2A at an excitation frequency of 255 Hz and FIG. 3 is schematic diagram of an alternate embodiment of the emission spectrometer of FIG. 1.

The critical feature of the present invention resides in the elimination of the "chopper" which was heretofore used to modulate the emission radiation from the electric discharge tube 10 to provide a higher frequency signal. Instead the optical signal from the discharge tube 10 is filtered and converted to an electrical signal which is amplified by an analog amplifier 24 for selective amplification of the electrical signal at essentially twice the excitation frequency of the input power supply 14. Although any excitation frequency may be used it is preferred to operate with a power supply excitation frequency of 255 Hz or greater. This results in an increase in sensitivity in detecting the presence of an impurity in the gas sample. The significance of the invention is best understood from the oscillograph traces of the output of the photomutiplier 22, which is a measure of the optical emission of the silent electric discharge tube 10, as shown in in FIG. 2A and 2B respectively. In FIG. 2A the variable frequency oscillator 18 is adjusted to a one to one ratio such that the excitation frequency of the input power supply is 60 Hz whereas in FIG. 2B the variable frequency oscillator 18 is adjusted such that the excitation frequency of the input power supply 14 equals 255 Hz. With the excitation frequency adjusted to 60 Hz the amplifier 24 is tuned to 120 Hz and with the excitation frequency adjusted to 255 Hz the amplifier 24 is tuned to 510 Hz. Each negative pulse shown in the oscillograph traces is indicative of an electric discharge ocurring between the electrodes in the electric discharge tube 10. In FIG. 2B the scale of the abcissa is 200 mv/div which is twice the scale of the absissa in FIG. 2A indicating a much larger signal peak for the negative pulses for a higher excitation frequency. Furthermore at higher excitation frequency the negative pulses do not return to the upper baseline as in FIG. 2A. As the excitation frequency increases the successive discharges in each half period increase with each successive discharge beginning before the preceding discharge recovers. In theory, as the excitation frequency is further increased the discharge pattern will approximate a square wave in which all noise is substantially eliminated thereby further increasing detection sensitivity. The optimum excitation frequency will depend upon the impurity gas to be analyzed and the output voltage of the ionization transformer 16. Too high a voltage can lead to breakdown and arcing whereas too low a voltage will render the discharge unstable. The output voltage of the transformer 16 should preferably be between 7000 volts and 25000 volts. The preferred excitation frequency range is 255 Hz to 5000 Hz. The flow rate of the sample gas stream passing into the discharge tube 10 may be up to 50 SCFH, preferably up to 10 SCFH and more preferably between 1–4 SCFH.

It should be apparent from the above description of the invention that by changing the wavelength selected by the optical filter 20, the spectrometer of the present invention may be made to analyze for any impurity that has a suitable emission line in the UV or visible spectrum. As an example, changing the optical wavelength from 337.1 nm to 308.0 nm would enable moisture to be analyzed whereas by changing the wavelength to 430.0 nm would permit methane to be analyzed. Moreover, the analysis can be performed using a gas stream of base gases other than argon. The operating pressure and the geometry of the discharge tube favor the excitation of the component of the gas mixture with the lower ionization potential. Nitrogen can be analyzed in argon because of the lower ionization potential of nitrogen relative to argon. Therefore, any base gas can be used which has a higher ionization potential than the impurity gas or vapor. Accordingly, nitrogen may readily be analyzed for its presence as an impurity in base gases other than argon such as, for example, helium (He), neon (Ne), and Krypton (Kr) respectively or mixtures thereof.

Figure 3:
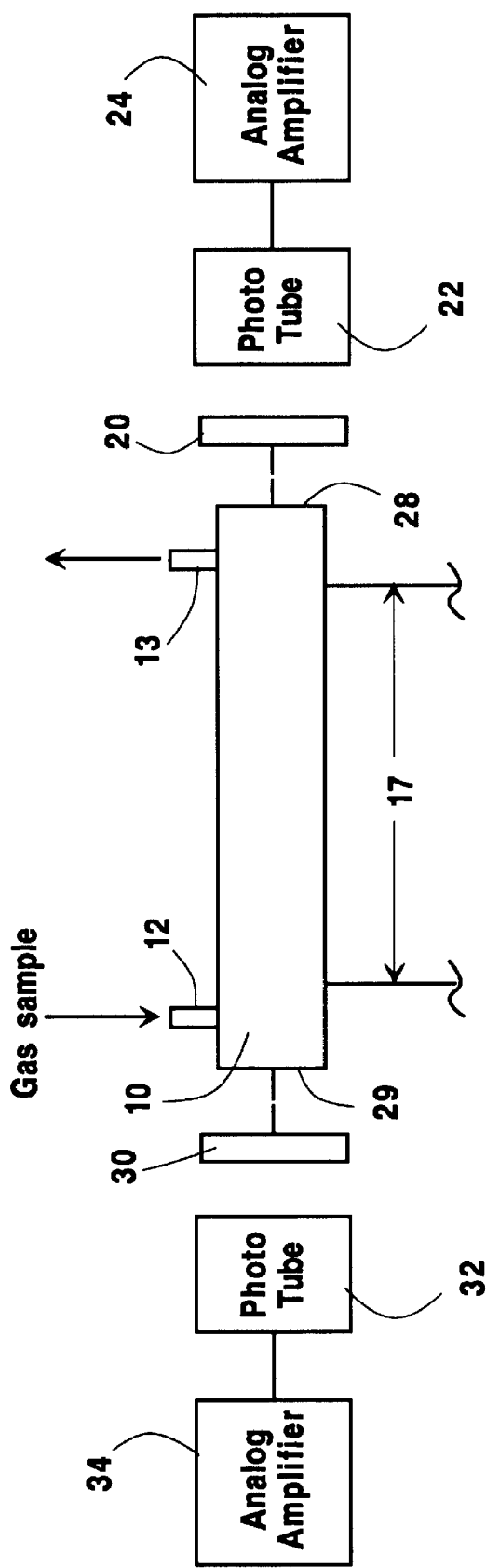

An alternate embodiment of the invention for analyzing for two impurity gases simultaneously from the same gas sample is schematically illustrated in FIG. 3. The arrangement is basically similar to that of FIG. 1 with identical reference numerals used to identify corresponding components. In the arrangement of FIG. 1, radiation emission is analyzed from one specific end 28 of the silent discharge tube 10 to measure the concentration of a specific gas impurity. The complementary opposite end 29 of the discharge tube 10 is used at the same time in the arrangement of FIG. 3 for analyzing the radiation emission spectrum for the presence of a second gas impurity independent of the analysis of the radiation emission from the end 28 of the discharge tube 10. An optical filter 30 is used having a wavelength corresponding to the second gas impurity of, for example, 308 nm if the second gas impurity is moisture while the optical filter 20 is selected to analyze for nitrogen or methane. Another photomultiplier tube 32 and analog amplifier 34 is used to duplicate the function of the photomultiplier 22 and analog amplifier 24 to analyze and measure the concentration of the second gas impurity simultaneous with the analysis of the first gas impurity. The analysis operation for each gas is independent of one another and is non-interfering. This arrangement is distinct from using, for example, a beam splitter to analyze for two gas impurities from the same emitted radiation.

What we claim is:

1. A gas emission spectrometer for analyzing and measuring low concentration levels of one or more gas/vapor impurities in a gas stream under continuous flow conditions comprising: an electric discharge source; means for feeding a gas sample through said electric discharge source at a preselected flow rate; power supply means for applying an alternating voltage across said discharge source at a predetermined excitation frequency and having sufficient peak voltage to sustain an electric discharge and generate emissive radiation from said gas stream over a wide radiation spectrum; means for optically filtering said emissive radiation to form an optical signal having a narrow radiation emission bandwidth corresponding to the stronger emission wavelength(s) of a preselected gas/vapor impurity in said gas sample; means for converting said optical signal into a corresponding electrical signal and analog amplifier means for selectively amplifying said electrical signal within a narrow frequency range centered at substantially twice said excitation frequency, wherein said gas stream impurity is selected from the group consisting of nitrogen and methane, a base gas is argon, said impurity to be analyzed is nitrogen and at said excitation frequency of 255 Hz or higher.

2. A gas emission spectrometer as defined in claim 1 wherein said nitrogen below 20 ppb can be detected.

3. A gas emission spectrometer as defined in claim 1 wherein said analog amplifier means is a lock-in analog amplifier.

4. A gas emission spectrometer as defined in claim 1 wherein said electric discharge source is a silent electric discharge tube.

5. A gas emission spectrometer as defined in claim 1 wherein said base gas is selected from the group consisting of argon, helium, krypton and mixtures thereof.

* * * * *